(12) United States Patent
Benedict et al.

(10) Patent No.: US 8,030,058 B1
(45) Date of Patent: Oct. 4, 2011

(54) AUTOMATED APPARATUS FOR PANCREATIC ISLET ISOLATION AND PROCESSING

(76) Inventors: Daniel J. Benedict, Chicago, IL (US); Lorna S. Mosse, Chicago, IL (US)

(*) Notice: Subject to any disclaimer, the term of this patent is extended or adjusted under 35 U.S.C. 154(b) by 1237 days.

(21) Appl. No.: 11/367,188

(22) Filed: Mar. 3, 2006

Related U.S. Application Data

(63) Continuation-in-part of application No. 10/056,662, filed on Jan. 23, 2002, now Pat. No. 7,045,349.

(60) Provisional application No. 60/263,273, filed on Jan. 23, 2001.

(51) Int. Cl.
*C12M 1/36* (2006.01)

(52) U.S. Cl. ............ 435/286.5; 435/286.1; 435/286.2; 435/286.3; 435/286.4; 435/286.6; 435/286.7

(58) Field of Classification Search ..... 435/286.1–286.7
See application file for complete search history.

(56) References Cited

U.S. PATENT DOCUMENTS

| | | | | |
|---|---|---|---|---|
| 4,167,450 A | * | 9/1979 | Chesbro et al. | 435/3 |
| 5,198,362 A | * | 3/1993 | Forsyth et al. | 435/254.1 |
| 6,361,995 B1 | * | 3/2002 | Konrad et al. | 435/325 |
| 6,365,385 B1 | * | 4/2002 | Opara | 435/178 |
| 2004/0248077 A1 | | 12/2004 | Rodriguez et al. | |

* cited by examiner

*Primary Examiner* — Michael Marcheschi
*Assistant Examiner* — Jameson Ma
(74) *Attorney, Agent, or Firm* — Neifeld IP Law, P.C.

(57) ABSTRACT

Advanced islet separation technology incorporates an automated method, automated control methodology, process control interface, and automated apparatus to separate (isolate) and process pancreatic islets in a tissue suspension in physiologic process solution, utilizing microprocessor control and/or microprocessor computer control and software programming (code) to interface and control the process temperature, fluid flow rate, pH, dissolved oxygen concentration, endotoxin concentration, dissolved nitric oxide concentration, nitric oxide synthase activity, proteolytic enzyme activity, and/or pressure of the islet containing physiologic process solution, the extent of islet separation, including real-time data acquisition and recording of process variables.

8 Claims, 5 Drawing Sheets

FIG. 4

AUTOMATED ISLET SEPARATION APPARATUS PROCESS CONTROL VALVE LOGIC
401

| ACTION | STATE | VALVE | | | | | | | | |
|---|---|---|---|---|---|---|---|---|---|---|
| FILL | OPEN | 104 | 116 | 126 | 132 | 139 | 154 | 180 | | |
| | CLOSED | 115 | 117 | 125 | 127 | 131 | 135 | 137 | 153 | |
| CIRCULATE AND RINSE | OPEN | 116 | 126 | 132 | 139 | 153 | 180 | | | |
| | CLOSED | 104 | 115 | 117 | 125 | 127 | 131 | 135 | 137 | 154 |
| DRAIN | OPEN | 104 | 116 | 126 | 132 | 137 | 180 | | | |
| | CLOSED | 115 | 117 | 125 | 127 | 131 | 135 | 139 | 153 | 154 |
| REFILL | OPEN | 104 | 116 | 126 | 132 | 139 | 154 | 180 | | |
| | CLOSED | 115 | 117 | 125 | 127 | 131 | 135 | 137 | 153 | |
| PANCREAS ADDITION IN DYNAMIC FLOW DIGESTION CHAMBER | OPEN | 115 | 125 | 126 | 132 | 139 | 153 | | | |
| | CLOSED | 104 | 116 | 117 | 180 | 127 | 131 | 135 | 137 | 154 |
| DIGESTION, SEPARATION AND CIRCULATION WITH DYNAMIC FLOW DIGESTION CHAMBER FORWARD FLOW | OPEN | 116 | 126 | 132 | 139 | 153 | 180 | | | |
| | CLOSED | 104 | 115 | 117 | 125 | 127 | 131 | 135 | 137 | 154 |
| DIGESTION, SEPARATION AND CIRCULATION WITH DYNAMIC FLOW DIGESTION CHAMBER REVERSE FLOW | OPEN | 115 | 117 | 125 | 127 | 132 | 139 | 153 | 180 | |
| | CLOSED | 104 | 116 | 126 | 131 | 135 | 137 | 154 | | |
| AUTOSAMPLE AND CIRCULATE | OPEN | 116 | 126 | 132 | 135 | 139 | 153 | 180 | | |
| | CLOSED | 104 | 116 | 118 | 126 | 128 | 132 | 137 | 154 | |
| DILUTE AND COLLECT | OPEN | 104 | 116 | 126 | 131 | 180 | | | | |
| | CLOSED | 115 | 117 | 125 | 127 | 132 | 135 | 137 | 139 | 153 | 154 |
| OXYGEN SPARGING ON | OPEN | 146 | | | | | | | | |
| OXYGEN SPARGING OFF | CLOSED | 146 | | | | | | | | |
| HELIUM SPARGING ON | OPEN | 149 | | | | | | | | |
| HELIUM SPARGING OFF | CLOSED | 149 | | | | | | | | |

AUTOMATED APPARATUS FOR PANCREATIC ISLET ISOLATION AND PROCESSING

CROSS-REFERENCE TO RELATED APPLICATIONS

This application is a continuation-in-part of U.S. patent application Ser. No. 10/056,662, filed on Jan. 23, 2002, now U.S. Pat. No. 7,045,349, which claims the benefit of U.S. Provisional Application No. 60/263,273, filed Jan. 23, 2001, the disclosures of which patent applications are incorporated by reference as fully set forth herein.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

The present invention relates to the isolation of pancreatic islets for transplantation into diabetic patients. In preferred embodiments, the invention presents Advanced Islet Separation Technology, an automated method of islet isolation (separation), an automated process control methodology, process control interface, and an automated apparatus to separate and process pancreatic islets in physiologic process solution utilizing microprocessor control and/or computer control of the process variables and automated apparatus, and the extent of islet separation. The invention may be uniformly applied to islets harvested from animals and mammals, either transgenic or non-transgenic.

The islets of Langerhans, endocrine tissue containing insulin producing beta cells, represent about one to two percent of the total mass of the human pancreas. Separation or isolation of the islets from the connective matrix and remaining exocrine tissue is advantageous and beneficial for laboratory experimentation and transplantation purposes. Islet transplantation is a most promising and minimally physiologically invasive procedure for treatment of type I diabetes mellitus. Transplanting islets rather than complete pancreatic tissue has the distinct advantages of ease of transplantation, and the elimination of the pancreatic exocrine function of the donor tissue involving secretion of digestive enzymes. Liberating islets from pancreatic exocrine tissue is the initial and crucial step that influences islet transplantations. The important objective in islet isolations is to provide sufficient numbers of viable functional and potent islets for transplantation.

Collagenases, metalloendoproteinases that cleave collagen into smaller peptide fragments, are zinc-containing enzymes that require divalent calcium as a cofactor for stabilization and optimal activity. Using traditional collagenases detrimentally affects pancreatic digestion due to the impurities present in the collagenase solutions. Traditional collagenase preparations are concentrated from bacterial (*Clostridium histolyticum*) culture supernatants. Roche, a manufacturer of molecular biochemicals, states that such collagenase preparations are heterogeneous, containing as many as 30 different enzymes, pigments, cellular debris, and endotoxins. The most significant liabilities of traditional collagenase are variability and endotoxin levels. In traditional collagenase, the primary enzymatic constituent is collagenase, classes I and II. Other proteases found include neutral protease, clostripain, elastase, trypsin, and aminopeptidase.

While larger scale islet separation from human pancreata has become possible with advances in technology, the current techniques cited herein fall short in terms of efficiency, and are inadequate for scale up or mass production in which many donor pancreata are processed at different research and transplantation centers, medical facilities, or commercial locations. In consideration of the lack of donor pancreata, current islet isolation techniques are also inadequate to continuously and repetitively batch process porcine pancreata, or pancreata from animals or mammals, transgenic or non-transgenic, to produce islets for xenotransplantation. In the current techniques cited herein and patents referenced herein exist limitations in the methodologies that may significantly affect the outcome of the islet separation process.

The method of mechanical tissue dissociation with glass marbles, steel balls or other sufficiently dense and solid objects, either by hand or with mechanical shaking (Ricordi shaker), may cause tissue damage and trauma to islets resulting from excessive shear stress during the separation process. While repetitive mechanical agitation and contacting the pancreas with solid objects effects tissue disruption aiding enzymatic digestion, such current practices in standard isolation techniques are subjective, and vary between research facilities and transplantation centers.

Although sonication has been employed to aid pancreatic tissue digestion, one certain limitation in this technique is the 'static' water bath that the 'bagged' pancreas is placed in. Interestingly, this technique is continued until the pancreas appears 'cracked', yet, no mention of the internal temperature of the pancreas is noted. Static digestion by any method offers no means of forced-convective heat transfer to maintain a constant processing temperature (cooling during sonication) of the digesting pancreas or the resulting tissue suspension, by the process solution. It is possible that the internal temperature of a bagged pancreas in such a static system exceeds 37 to 40 degrees C., a temperature considered optimal for functional enzymatic digestion, yet, minimal in thermal shock and deactivation of islets due to elevated temperature. A statically digested pancreas in a bag offers no opportunity to maintain a controlled pancreatic processing temperature. This method presents no opportunity to dilute the tissue suspension, which precludes a real-time method to control, deactivate, or inhibit the digestive enzymes in the processing solution, during islet separation and processing, in the dilution and collection phase.

At the XVIII International Congress of the Transplantation Society, Aug. 27-Sep. 1, 2000 in Rome, Italy, advances in pancreatic islet cell transplantation procedures were reviewed and discussed. Existing limits of transplantation and novel approaches to achieving tolerance were evaluated. It was noted that success of recent transplantations (Edmonton Protocol) might certainly be due to the use of immunosuppression that was not toxic to beta cells. Avoiding the use of corticosteroids, induction therapy with anti-IL-2 antibody, and low-dose tacrolimus and sirolimus maintenance were undoubtedly key factors in non-rejection and continued islet tolerance. The quality of the purified islets also contributed to the success of the transplantations, yet, acquired by tedious and laborious manual methods lacking in process control methodology and neglecting important process variables. Current challenges were also assessed, specifically, the standardization of islet separation technology, and the need to development a standardized, reproducible, and automated method to separate and produce high-quality islet cells.

The background art is characterized by U.S. Pat. Nos. 5,273,904; 5,322,790; 5,377,790; 5,424,209; 5,612,188; 5,834,005; 5,837,738; 5,853,976; 5,879,939; 5,919,703; 5,919,775; and 5,952,215; and U.S. Patent Application No. 2004/0248077; the disclosures of which patents and application are incorporated by reference as if fully set forth herein. The background art is also characterized by the following articles, the disclosures of which are incorporated by reference as if fully set forth herein: Bond and Van Wart, Biochemistry, 23:3077, 1984, and Biochemistry, 23:3085-3091, 1984; D. Scharp, World Journal of Surgery 8:143-151, 1984; Linetsky et al., Transplant Proc., 30(2):345-346, March 1998; Vargas et al., Transplantation, 65(5): 722-727, Mar. 15, 1998; Jahr et al., J. Mol. Medicine (Berlin), 77(1):118-120, January 1999; and Eckhardt et al., J. Mol. Medicine (Berlin), 77(1): 123-125, January 1999.

Presently there exists no process control method or device for islet separation that takes into account and crucial process variables that may be controlled to optimize islet isolation while standardizing and automating the islet separation process. Importantly, separation and processing variables have been omitted in background art methods and devices which compromise the reproducibility and repeatability of the islet separation process from location to location. Objectively applying advanced process control methodology disclosed herein and automating the islet isolation process with the process control technology and automated apparatus disclosed herein can optimize the islet separation process.

BRIEF SUMMARY OF THE INVENTION

In a preferred embodiment, the present invention relates to the application of advanced control methodology and process control technology, incorporating an automated method of islet separation (isolation) and processing, utilizing microprocessor and/or computer control and software programming, to control the process variables and interface the process control methodology to the automated islet separation apparatus, via an electrical (electronic) interface and a graphic user interface, and includes real-time data acquisition (DAQ) and recording of the process variables. Process variables that influence the islet separation process are preferably incorporated into the automated method of islet separation by integrating automated control of the process variables through the process control interface to the islet separation apparatus, utilizing an analog and digital (A/D) electrical (electronic) interface with feedback from and control of the islet separation apparatus. Process variables that influence the islet separation process are the physiologic process solution, the process temperature (T), the process flowrate (F), the negative logarithm of the hydrogen ion activity (pH [potential of hydrogen]), the dissolved oxygen (DO) concentration, the dissolved nitric oxide (NO) concentration, the dissolved carbon dioxide ($CO_2$) concentration, the digestive enzyme (PE) activity, the endotoxin (E) concentration, the antibiotic (A) concentration, and the pressure (P) of the islet containing physiologic process solution. By controlling selected variables that influence the reproducibility and repeatability of the islet separation process, the present invention is superior to the currently employed and subjectively standard islet isolation techniques, which neglect process control of the important and essential process variables.

In a preferred application of the automated method of islet separation utilizing the automated islet separation apparatus, a single researcher performs the islet isolations. Once a pancreas is suitable prepared and made ready for islet separation processing (U.S. Pat. No. 5,322,790, U.S. Pat. No. 5,853,976, both previously incorporated herein by reference), the researcher uses the automated islet separation method disclosed herein to start the automated islet separation apparatus with a single command via the electrical (electronic) and/or graphic user interface, initiating the fill, circulate and rinse cycle. After the initial rinse cycle, and the rinse solution is discarded, the islet separation apparatus again fills with physiologic solution and the method and apparatus then pause in operation (for a programmed time) until the pancreas is loaded in the dynamic flow digestion chamber.

After pancreas addition, once the dynamic flow digestion chamber is sealed, the automated method continues (after the programmed time) or the researcher restarts the automated method of islet separation and the automated islet separation apparatus with a single command via the electronic or graphic user interface, and monitors the process via the electrical (electronic) and graphic user interface (computer display). Once the automated islet separation method continues or the islet separation apparatus is restarted, the islet separation apparatus automatically adjusts, attains, maintains, regulates, and controls the desired, preset, and programmed values of the process variables during the digestion, separation, and circulation phase. In a preferred embodiment, the process variables are the programmed (setpoint) process temperature (T), the programmed (setpoint) process flowrate (F), the programmed (setpoint) potential hydrogen (pH), the programmed (setpoint) dissolved oxygen (DO) concentration, the dissolved nitric oxide (NO) concentration, the dissolved carbon dioxide ($CO_2$) concentration, the programmed (setpoint) digestive enzyme (PE) activity, the endotoxin (E) concentration, the antibiotic (A) concentration, and the pressure (P) of the islet containing physiologic process solution, or a subset of these process variables.

At the end of the digestion, separation, and circulation phase of islet processing, when the desired extent of islet separation is achieved (using the programmed [setpoint] values), the automated islet separation apparatus cycles into the dilution and collection phase. During the dilution and collection phase, the methodology disclosed herein is employed to control, deactivate, and inhibit the digestive effects of proteolytic enzymes and tissue dissociating agent, collagenase (e.g., Liberase), protecting the islets from unnecessary degradation during dilution and collection. Quite simply, during dilution and collection, collagenase is preferably inhibited by the addition of chelators of divalent cations such as citrate, EDTA, or EGTA.

In another preferred embodiment, metalloendoproteinase activity is inhibited by cysteine, tetracycline, and doxycycline, in accordance with the teachings of Smith Jr. et al., Annals NY Acad Sci 732:436-438, 1994, incorporated herein by reference. Throughout the dilution and collection phase, the fundamental process variables are preferably controlled at the programmed (setpoint) values. During this phase of islet processing, the islet separation apparatus preferably dilutes and autocollects the islet containing physiologic process solution by means of the automated islet autocollector.

In a preferred embodiment, the researcher may at any time alter, control, stop, and restart the process, if necessary, due to unforeseen disturbances. While the islet separation process is fully automated, it is still an automated batch process that is fully under the researcher's control via the electrical (electronic) and graphic user interface. Ultimately, in a preferred embodiment, the process needs no manual intervention and the entire separation process, after the loading of the pancreas into the dynamic flow digestion chamber, proceeds by the automated method. The automated method of islet separation, the automated islet separation apparatus, and the process variables are preferably microprocessor and/or computer controlled, and the entire islet separation process starting with the fill, circulate and rinse cycle, the pancreas addition proceeding through digestion, separation and circulation, and ending with the dilution and collection phase may be accomplished automatically via the setpoint values, or with start stop commands to process controllers and pumps and or keystrokes or mouse clicks, or touch screen commands.

During automated islet separation processing, specifically the digestion, separation and circulation phase, the islet containing physiologic process solution is preferably monitored via autosampled aliquots of the process solution. Depending on the level of sophistication required by the individual researcher, research facility, or transplantation center, the extent of pancreatic digestion and islet separation monitored in real-time may be accomplished either manually via autosampled aliquots, staining, and image analysis software, or automated on-line via integration of a flow through sample cell, autosampling, staining, and image analysis software. Preferably, during the islet separation, the endotoxin concentration of the islet containing physiologic process solution is monitored, recorded and controlled in real-time via the same autosampled aliquot.

In a preferred embodiment, process control and data acquisition of the automated method of islet separation and the automated islet separation apparatus is accomplished with microprocessor controllers and/or data loggers and/or a windows based (Win98) microprocessor computer (PC) operating in the LabView graphical software-programming environment (G), for example. The microprocessor computer (PC) is preferably equipped with analog and digital solid-state electrical (electronic) input output control boards that are electrically (electronically) interfaced to various analog and digital input output control hardware (modules) via sensors and electrical (electronic) connections. Islet separation process data are preferably collected in real-time and the researcher is presented with an electrical (electronic) and/or graphical interface that contains an interactive process flow-sheet displaying system status and processing data, which accepts user input and feedback to the process. Pumps, valves, thermocouples, sensors, probes, and transducers may be located on a graphical process flowsheet (computer display) and correspond to their actual physical location on the automated islet separation apparatus. The software may be programmed to automatically control the automated islet separation apparatus and the process variables at the programmed set points; yet, the researcher may at any time manually override the process. Islet separation process data are preferably acquired real-time during islet isolation from the process sensors and process controllers and microprocessor computer (PC) and logged in a data file for post-processing analysis, quality assurance, validation, and regulatory purposes.

Analog output process sensors, preferably including thermocouples, dissolved oxygen probe (sensor), pH probe (sensor), nitric oxide probe (sensor), carbon dioxide probe (sensor), endotoxin probe (sensor), process pump tachometer (flowrate), and pressure transducer (sensor), are preferably interfaced to signal conditioning input modules which input process data through the electrical (electronic) interface to the microprocessor controllers and the microprocessor computer (PC). The process pump speed (i.e. flowrate) is preferably controlled by analog or digital output from a microprocessor or computer (PC) through a signal conditioning output module and the electrical (electronic) interface. The process temperature (T), the process flowrate (F), the potential hydrogen (pH), the dissolved oxygen (DO) concentration, the dissolved nitric oxide (NO) concentration, the endotoxin (E) concentration, the proteolytic enzyme (PE) activity, the antibiotic (A) concentration, and the pressure (P) are preferably controlled by feedback from process sensors and analog and digital output from the microprocessor controllers and/or the microprocessor computer (PC) via analog and digital and solid state relays (SSR) through the electrical (electronic) interface. Analog and digital output from a microprocessor computer (PC) or programmable logic controller (PLC) via the analog-digital (A/D) interface through the electrical (electronic) interface is preferably used to activate electric solenoid valves controlling the process solution flow and flow direction. The process solution flow and direction of fluid flow of the automated islet isolation apparatus may be operated under electrical control via the electrical (electronic) and graphical interface or manual control and the graphical user interface.

Other operating systems such as WinXP, Win2000, WinNT, Win95, Win3.1, Linux, Warp, OS-2, or Mac OS for example, and other software-programming environments, Fortran, Pascal, C, C+, C++, Basic, Visual Basic, Java, HTML, or VRML for example, as well as PLCs and or programmable microprocessors (non PC) may be utilized to interface the automated control methodology and automated islet separation apparatus. Microprocessor controllers and or microprocessor computer (PC) and or programmable logic controller (PLC) may also be employed for automating the motion control of the autosampler, autocollector, and dynamic flow digestion chamber. General-purpose input output boards (GPIB) and/or RS-232 (or RS 485, USB, or Firewire) inputs and outputs may also be employed to control the operation of the automated islet separation apparatus including data acquisition.

It is one object of a preferred embodiment of this invention to present Advanced Islet Separation Technology and apply the technology to pancreatic islet separation (isolation) and processing. Advanced Islet Separation Technology preferably incorporates advanced control methodologies to control and monitor the critical process variables that affect the reproducibility and repeatability of islet separation processes from location to location.

Specifically, in a preferred embodiment, the present invention utilizes process control methodology and applies it to pancreatic islet isolation, uniquely incorporating an automated method, automated control methodology, process control interface, and an automated apparatus to separate and process pancreatic islets in physiologic process solution.

More particularly, in a preferred embodiment, this invention utilizes process variable setpoints employing microprocessor controllers, and/or a microprocessor computer control and software programming (code), to automate and interface the process control methodology, on-line in real-time, to control the process temperature (T), the process flowrate (F), the potential hydrogen (pH), the dissolved oxygen (DO) concentration, the dissolved nitric oxide (NO) concentration, the dissolved carbon dioxide (CO2) concentration, the digestive (proteolytic) enzyme (PE) activity, the endotoxin (E) concentration, the antibiotic (A) concentration, and/or the pressure (P) of the islet containing physiologic process solution during islet separation and processing, by means of an analog and/or digital electrical (electronic) interface, with feedback from the process sensors and control of the automated islet separation apparatus by the microprocessor controllers and/or computer and software code.

In a preferred embodiment, this invention provides on-line in real-time, process data acquisition and recording of the process variables during islet separation and processing, via an analog and digital electrical (electronic) interface and input from the process sensors in the islet separation apparatus.

In a preferred embodiment, this invention incorporates real-time image analysis to determine the extent of pancreatic digestion and islet separation to control the digestion time, utilizing image analysis software. Real-time image analysis may be accomplished either by discrete autosampling and manually staining utilizing microscopy and image analysis, or automated via a flow through sample cell and staining, utilizing discrete on-line image analysis, via an analog and digital electrical (electronic) interface and input to the islet separation apparatus.

In a preferred embodiment, this invention also provides a modified and improved temperature controlled, dynamic flow digestion chamber, incorporating forward fluid flow and reversing fluid flow, and rotary motion (or linear motion, or eccentric motion) with self-contained sonic transducers and sonication applied to the dynamically flowing islet containing processing fluid to aid tissue digestion, via an analog and digital electrical (electronic) interface and input to the islet separation apparatus (and/or dynamic flow digestion chamber).

Provided by preferred embodiments of this invention are methods to control, deactivate, and inhibit the digestive effects of the proteolytic enzymes utilized to digest pancreatic connective tissue (collagen) at the end of the digestion, separation and circulation phase, during the dilution and collection phase.

In a further preferred embodiment, this invention further provides a method to control and monitor in real-time, the nitric oxide concentration and/or nitric oxide synthase activity present in the islet containing physiologic process solution during islet separation and processing.

In another preferred embodiment, this invention further provides a method to monitor and control in real-time via discrete analysis, the endotoxin concentration present in the islet containing physiologic process solution during islet separation and processing.

In another preferred embodiment, this invention further provides a method to monitor and control in real-time, the carbon dioxide concentration present in the islet containing physiologic process solution during islet separation and processing.

In a preferred embodiment, the invention is an apparatus for isolating islets from a pancreatic tissue, said apparatus comprising: a heated feed tank; a reactor for containing a physiologic process solution having a dissolved oxygen concentration, a dissolved nitric oxide concentration, a pH, a temperature, a pressure, an endotoxin concentration, and a dissolved carbon dioxide concentration, said reactor comprising a flow loop that connects a digestion chamber, a sparging vessel, and a process pump, said flow loop being connected through a first valve to said heated feed tank, said process pump being operative to circulate said physiologic process solution through said reactor; a process controller; a sensor block that is located on said flow loop upstream from said digestion chamber, said sensor block having a plurality of sensors that send signals to said process controller, said sensor block comprising a dissolved oxygen sensor for sensing said dissolved oxygen concentration, a dissolved nitric oxide sensor for sensing said dissolved nitric oxide concentration, a pH sensor for sensing said pH, a temperature sensor for sensing said temperature, a pressure sensor for sensing said pressure, an endotoxin sensor assembly for sensing said endotoxin concentration, and a carbon dioxide sensor for sensing said dissolved carbon dioxide concentration; a process cooler that is located on said flow loop and a process heater that is located on said flow loop; a plurality of solution pumps comprising a digestive enzyme solution pump for pumping a digestive enzyme solution from a digestive enzyme solution reservoir into said flow loop, an endotoxin neutralizing protein solution pump for pumping an endotoxin neutralizing protein solution from an endotoxin neutralizing protein solution reservoir into said flow loop, an acid solution pump for pumping an acid solution from an acid solution reservoir into said flow loop, and a base solution pump for pumping a base solution from a base solution reservoir into said flow loop; a source of oxygen gas controlled by a oxygen gas valve for introducing a stream of oxygen gas into said sparging vessel, a source of carbon dioxide gas controlled by a carbon dioxide gas valve for introducing a stream of carbon dioxide gas into said sparging vessel, and a source of an inert gas controlled by an inert gas valve for introducing a stream of inert gas into said sparging vessel; and an auto-collector that is connected to said flow loop for collecting the islets; wherein said process controller is operative to compare the dissolved oxygen concentration in said physiologic process solution to a dissolved oxygen setpoint and activate either said oxygen gas valve to add dissolved oxygen or said inert gas valve to remove dissolved oxygen, to compare said dissolved carbon dioxide concentration to a dissolved carbon dioxide setpoint and activate said inert gas valve to remove dissolved carbon oxide, to compare said dissolved nitric oxide concentration to a dissolved nitric oxide setpoint and activate said inert gas valve to remove dissolved oxygen and inhibit nitric oxide formation, to compare said pH to a pH setpoint and activate either said acid solution pump to reduce said pH or said base solution pump to increase said pH, to compare said temperature to a temperature setpoint and to activate either said process cooler to decrease said temperature or said process heater to increase said temperature, to compare said endotoxin concentration to an endotoxin concentration setpoint and activate said endotoxin neutralizing protein solution pump and to compare said dissolved carbon dioxide concentration to a dissolved carbon dioxide concentration setpoint and increase said dissolved carbon dioxide concentration by introducing said stream of carbon dioxide gas into said sparging vessel. Preferably, said plurality of solution pumps further comprise a proteolytic control means selected from the group consisting of an amino acid solution pump for pumping an amino acid solution from an amino acid solution reservoir into said flow loop and a chelator solution pump for pumping a chelator solution from an chelator solution reservoir into said flow loop; and wherein said process controller is operative to compare said proteolytic enzyme activity to a proteolytic enzyme activity set point and activate either said amino acid pump or said chelator solution pump. Preferably, said plurality of solution pumps further comprise a dissolved nitric oxide control means selected from the group consisting of an antibiotic solution pump for pumping an antibiotic solution from an antibiotic solution reservoir into said flow loop and a dextran or heparin solution pump for pumping a dextran solution or a heparin solution from a dextran solution or a heparin solution reservoir into said flow loop; and wherein said process controller is operative to compare said dissolved nitric oxide concentration to a dissolved nitric oxide concentration set point and activate either said antibiotic solution pump or said dextran or heparin solution pump. Preferably, moving means are provided that are operative to rotate, move linearly or move eccentrically said digestion chamber, valve means are provided that are operative to circulate the physiologic process solution through said digestion chamber in a forward direction and in a reverse direction and transducer means are provided that are operative to cause sonication of the physiologic process solution circulating through said digestion chamber.

In another preferred embodiment, the invention is a method for isolating islets from pancreatic tissue, said method comprising: filling a reactor disclosed herein with a first portion of said physiologic process solution; circulating said first portion of said physiologic process solution through said reactor; draining said first portion of said physiologic process solution from said reactor to produce a rinsed reactor; refilling said reactor with a second portion of said physiologic process solution by circulating said second portion of said physiologic process solution through said reactor; pausing the circulation of said second portion of said physiologic process solution through said reactor; adding the pancreatic tissue to said digestion chamber; restarting the circulation of said second portion of said physiologic process solution through said reactor and performing real-time data acquisition by said plurality of sensors; sampling said second portion of said physiologic process solution to determine whether the islets that have been liberated from the pancreatic tissue into said second portion of said physiologic process solution; when the islets have been liberated from the pancreatic tissue into said second portion of said physiologic process solution, cycling said reactor to affect dilution and collection of the islets. Preferably, circulation of said second portion of said physiologic process solution through said reactor comprises: flowing said second portion of said physiologic process solution through said reactor in a forward direction; and/or flowing said second portion of said physiologic process solution through said reactor in a reverse direction.

In yet another preferred embodiment, the invention is a method for isolating islets from pancreatic tissue, said method comprising: circulating a physiologic process solution through a reactor having a flow loop that connects a digestion chamber into which said pancreatic tissue has been deposited, a sparging vessel and a process pump, said physiologic process solution having a dissolved oxygen concentration, a dissolved nitric oxide concentration, a pH, a temperature and an endotoxin concentration; performing real-time data acquisition by means of a plurality of sensors that are exposed to physiologic process solution as it circulates through said flow loop, said plurality of sensors comprising a dissolved oxygen sensor for sensing said dissolved oxygen concentration, a dissolved nitric oxide sensor for sensing said dissolved nitric oxide concentration, a pH sensor for sensing said pH, a temperature sensor for sensing said temperature, and an endotoxin sensor for sensing said endotoxin concentration; automatically controlling said dissolved oxygen concentration, said dissolved nitric oxide concentration, said pH, said temperature and said endotoxin concentration; sampling said physiologic process solution to determine whether the islets that have been liberated from the pancreatic tissue into said physiologic process solution; when the islets have been liberated from the pancreatic tissue into said physiologic process solution, collecting the islets.

In a further preferred embodiment, the invention is an apparatus for isolating islets from pancreatic tissue, said apparatus comprising: means for circulating a physiologic process solution through a reactor having a flow loop that connects a digestion chamber into which said pancreatic tissue has been deposited, a sparging vessel and a process pump, said physiologic process solution having a dissolved oxygen concentration, a dissolved nitric oxide concentration, a pH, a temperature and an endotoxin concentration; means for performing real-time data acquisition by means of a plurality of sensors that are exposed to physiologic process solution as it circulates through said flow loop, said plurality of sensors comprising a dissolved oxygen sensor for sensing said dissolved oxygen concentration, a dissolved nitric oxide sensor for sensing said dissolved nitric oxide concentration, a pH sensor for sensing said pH, a temperature sensor for sensing said temperature, and an endotoxin sensor for sensing said endotoxin concentration; means for automatically controlling said dissolved oxygen concentration, said dissolved nitric oxide concentration, said pH, said temperature and said endotoxin concentration; means for sampling said physiologic process solution to determine whether the islets that have been liberated from the pancreatic tissue into said physiologic process solution; means for collecting the islets when the islets have been liberated from the pancreatic tissue into said physiologic process solution.

In another embodiment, the invention is, in combination, an apparatus for collecting a subpopulation of cells from a digested organ or other biological material, said apparatus comprising: a reactor having a first chamber (e.g., a digester) adapted to receive an organ or other biological material to be digested in order to release a subpopulation of cells and a second chamber (e.g., an auto-collector) operatively connected to said first chamber, said second chamber adapted to receive said subpopulation of cells; and a computer operatively connected to said reactor to provide for operative control of at least three parameters of an environment within said apparatus, in order to facilitate said process of collecting a subpopulation of cells from a digested organ or other biological material. Preferably, said at least three parameters are selected from the group consisting of temperature, pressure, pH, dissolved oxygen concentration, a dissolved nitric oxide concentration, endotoxin concentration, dissolved carbon dioxide concentration, flowrate and antibiotic concentration. Preferably, said first and second chambers are operatively connected one to another via a plurality of conduits. Preferably, said first chamber and said second chamber form a flow loop, which allows for fluid flow through said first and second chambers and said plurality of conduits. Preferably, said flow loop further includes a heat exchanger, and a process pump, said heat exchanger and said process pump operatively connected to said first chamber and said second chamber via said plurality of conduits. Preferably, said combination further comprises a plurality of valves adapted to be opened or closed, each of said plurality of valves operatively connected to one of said plurality of conduits. Preferably, said computer adapted to control the opening and closing of each of said plurality of valves. Preferably, the opening and closing of each of said plurality of valves is controlled by manual manipulation of said computer by a user. Preferably, said computer further comprises a graphical user interface to facilitate manual manipulation of said computer by said user. Preferably, said computer is operatively connected to said reactor by means of an analog, digital and connector block interface.

Further aspects of the invention will become apparent from consideration of the drawings and the ensuing description of preferred embodiments of the invention. A person skilled in the art will realize that other embodiments of the invention are possible and that the details of the invention can be modified in a number of respects, all without departing from the concept. Thus, the following drawings and description are to be regarded as illustrative in nature and not restrictive.

BRIEF DESCRIPTION OF THE SEVERAL VIEWS OF THE DRAWINGS

The features of the invention will be better understood by reference to the accompanying drawings which illustrate presently preferred embodiments of the invention. In the drawings:

FIG. 4 is a schematic process control valve logic diagram of the automated islet separation apparatus showing the valve logic of the automated method according to one preferred embodiment of the invention.

Figure 1:
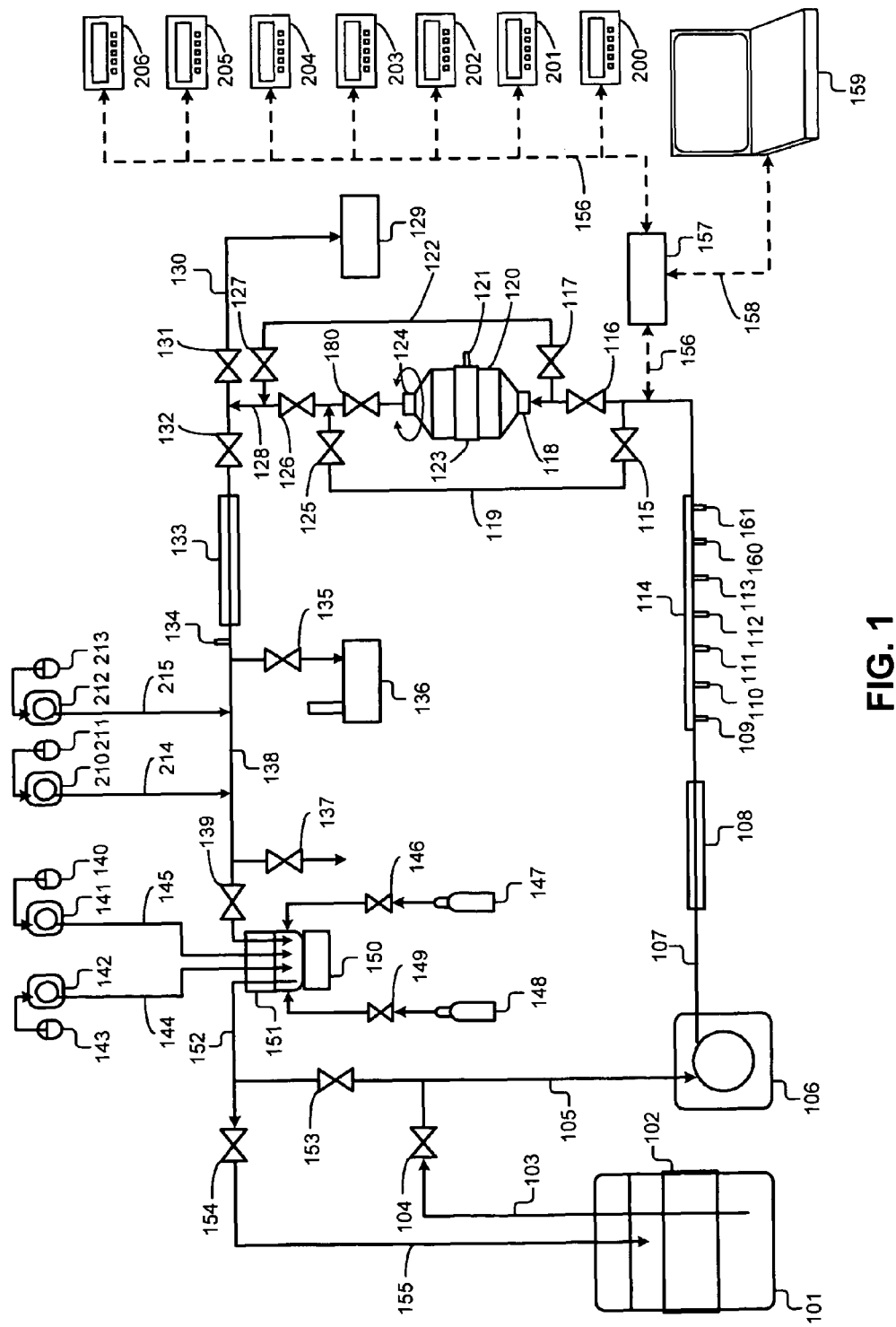
FIG. 1 is a schematic process flowsheet of the automated islet separation apparatus showing the various components of the automated islet separation apparatus and the microprocessor controllers and microprocessor computer interfaced to the automated apparatus according to one preferred embodiment of the invention.

The following reference numerals are used to indicate the parts and environment of the invention on the drawings:

101 feed tank
102 tank heater
103 first process tube, first process conduit
104 first process valve
105 second process tube, second process conduit
106 process pump
107 third process tube, third process conduit
108 heat exchanger
109 dissolved oxygen sensor
110 nitric oxide sensor
111 pH sensor
112 temperature sensor
113 pressure sensor
114 sensor block
115 second process valve
116 third process valve
117 fourth process valve
118 first rotary coupling
120 digestion chamber
121 digester temperature sensor
123 first process heater
124 second rotary coupling
125 fifth process valve
126 sixth process valve
127 seventh process valve
128 fourth process tube, fourth process conduit
129 auto-collector
130 seventh process tube, seventh process conduit
131 eighth process valve
132 ninth process valve
133 second process heater, second process heat exchanger
134 second temperature sensor
135 tenth process valve
136 auto-sampler
137 eleventh process valve
138 fifth process tube, fifth process conduit
139 fifteenth process valve
140 acid reservoir
141 acid pump
142 base pump
143 base reservoir
144 base addition tube
146 oxygen control valve
147 oxygen tank
148 helium tank
149 helium control valve
150 stirring plate
151 collection vessel, collection chamber
152 sixth process tube, sixth process conduit
153 twelfth process valve
154 thirteenth process valve
155 sixth process tube, sixth process conduit
156 first wiring
157 analog and digital and connector block interface
158 second wiring
159 computer, microprocessor computer
159A memory
159B software code
159C user interface
159D graphical display
160 endotoxin sensor
161 carbon dioxide sensor
180 fourteenth process valve
200 temperature controller
201 pH controller
202 dissolved oxygen controller
203 endotoxin neutralizing protein controller
204 proteolytic enzyme neutralization controller
205 nitric oxide controller
206 carbon dioxide controller, microprocessor process meter
210 endotoxin neutralizing protein pump
211 ENP solution reservoir
212 PEN pump
213 PEN solution reservoir
214 ENP addition tube
215 PEN addition tube
302 fill step
303 circulation and rinse step
304 drain step
305 refill step
306 first pause step
307 pancreas addition step
308 data acquisition step
309 digestion/separation/circulation step
310 restart step
311 second pause step
312 autosampling step
313 cycle step
314 auto-collection step
315 end step

DETAILED DESCRIPTION OF THE INVENTION

In a preferred embodiment, the invention is directed at an improved and automated method of islet isolation (separation), employing automated process control methodology, a process control interface, and automated apparatus to separate and process pancreatic islets in physiologic process solution utilizing microprocessor controllers and microprocessor computer control (PC) of the process variable setpoints and automated apparatus, including real-time process data acquisition. In another preferred embodiment, the invention is also directed at a dynamic flow digestion chamber incorporating forward fluid flow and reversing fluid flow, rotary motion (or linear motion, or eccentric motion) with self-contained sonic transducers incorporated in the dynamic flow digestion chamber with sonication applied to the dynamically flowing islet containing processing solution.

FIG. 1 illustrates a schematic flowchart of the interaction of the various components of the automated islet isolation apparatus according to one preferred embodiment of the invention. As shown in FIG. 1, in this embodiment, the physiologic process solution flows from feed tank 101 incorporating tank heater 102 through first process tube 103 through first process valve 104 through second process tube 105 through process pump 106 through third process tube 107 through process heat exchanger 108 through sensor block 114 that contains process sensors, including dissolved oxygen sensor 109, nitric oxide sensor 110, pH sensor 111, temperature (thermocouple) sensor 112, pressure (transducer) sensor 113, endotoxin sensor 160, carbon dioxide sensor 161, and in the forward flow direction through third process valve 116 through first rotary coupling 118 through the dynamic flow digestion chamber 120 incorporating digester temperature (thermocouple) sensor 121 and first process heater 123 through second rotary coupling 124 through fourteenth process valve 180 through sixth process valve 126 through fourth process tube 128 through ninth process valve 132 through second process heat exchanger 133 through temperature (thermocouple) sensor 134 through fifth process tube 138 through fifteenth process valve 139 into collection vessel 151 on stirring plate 150 through sixth process tube 152 through thirteenth process valve 154 through sixth process tube 155 returning to the feed tank 101 during the circulation and rinse phase of islet processing. After pancreas addition to the dynamic flow digestion chamber, during the digestion, separation, and circulation phase of islet processing, the physiologic process solution flows from sixth process tube 152 through twelfth process valve 153 again through second process tube 105 forming a process loop or flow loop.

FIG. 1 also illustrates according to one preferred embodiment of the invention the process sensors (previously described) and the microprocessor controllers (e.g., setpoint enabled) temperature controller 200, pH controller 201, dissolved oxygen controller 202, endotoxin neutralizing protein (ENP) controller 203, proteolytic enzyme (collagenase) neutralization (PEN) controller 204, nitric oxide controller 205, and carbon dioxide meter/controller 206, interconnected by first electrical (electronic) wiring 156, analog and digital and connector block interface 157, and microprocessor computer 159 utilizing 157 interconnected by second electrical (electronic) wiring 158, oxygen control valve 146, oxygen tank 147, helium tank 148, helium control valve 149, acid reservoir 140, acid pump 141, acid addition tube 145, base pump 142, base reservoir 143, base addition tube 144, endotoxin neutralizing protein (ENP) pump 210, ENP solution reservoir 211, ENP addition tube 214, (digestive) proteolytic enzyme neutralization (PEN) pump 212, and PEN solution reservoir 213, PEN addition tube 215, which are preferably employed to control the chemical character of the process solution at the setpoints during islet isolation and separation processing. Periodic sampling of the process solution is preferably accomplished via sampling (tenth) process valve 135 and auto-sampler 136. When the pancreas has been sufficiently digested, auto-collection of the islets and the process solution is preferably accomplished when process solution flows through eight process valve 131 through seventh process tube 130 and into the auto-collector 129.

Figure 2:
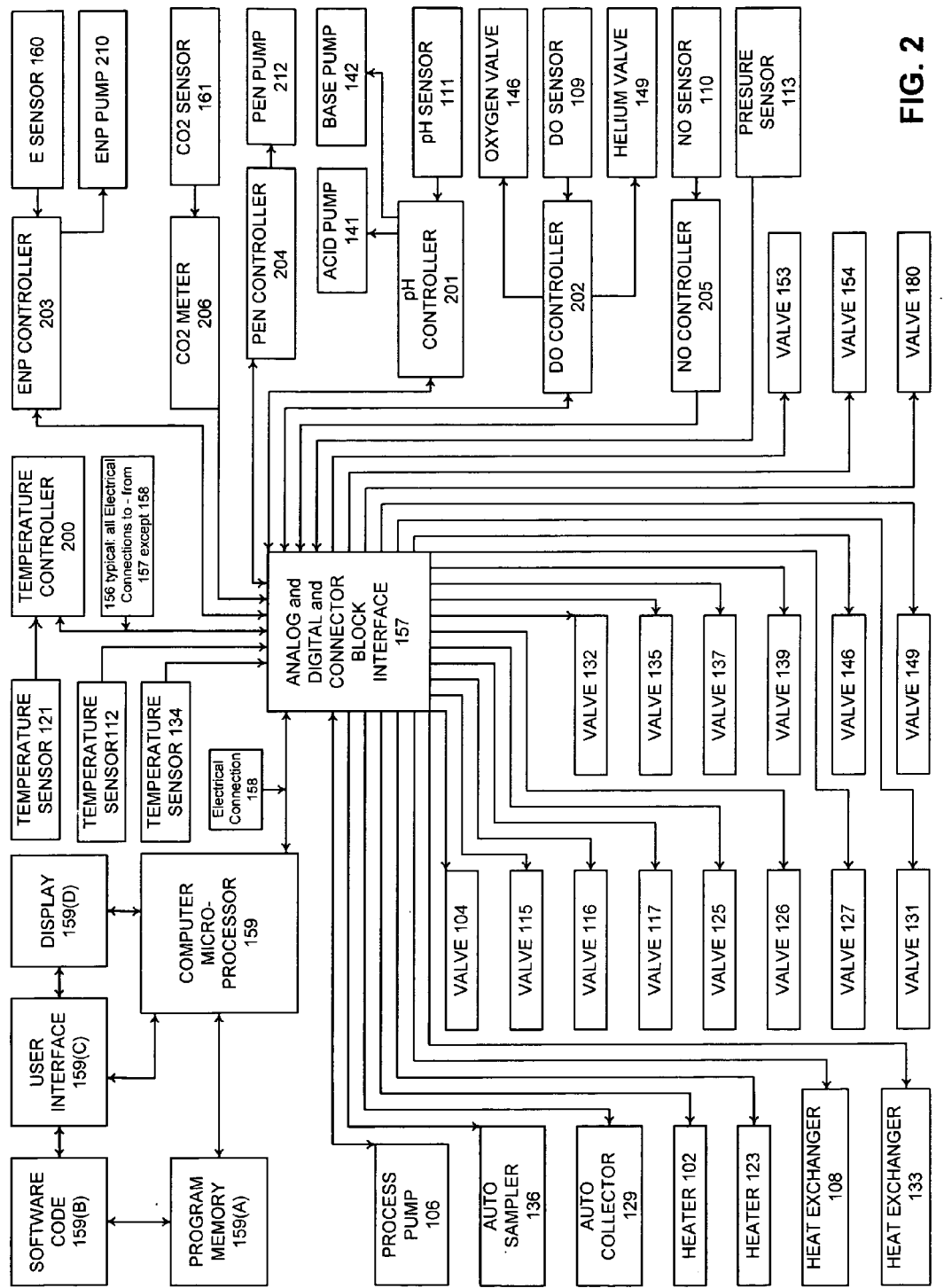
FIG. 2 is a schematic block diagram of the automated islet separation apparatus showing the interaction of the components of the automated apparatus including the analog and digital electrical (electronic) interface and the microprocessor controllers and the microprocessor computer according to one preferred embodiment of the invention.

FIG. 2 illustrates a schematic block diagram of the interaction of the various components of the automated islet isolation apparatus, electrical connections and wiring according to one preferred embodiment of the invention. Electrical process connections 156 preferably interface the process sensors 109, 110, 111, 112, 113, 121, 134, 160, 161 (previously presented in FIG. 1), the microprocessor process controllers 200, 201, 202, 203, 204, 205 (previously presented in FIG. 1), and the microprocessor process meter/controller 206, (previously presented in FIG. 1) through analog and digital and connector block interface 157 to the automated islet separation apparatus. A microprocessor computer (PC) 159 is employed to control the electric (solenoid) process valves 104, 115, 116, 117, 125, 126, 127, 131, 132, 135, 137, 139, 146, 149, 153, 154, 180 (previously presented in FIG. 1) and to record the processing data via real-time process data acquisition (DAQ—sensor output from the sensors and microprocessor process controllers and microprocessor process meters) through electrical (electronic) process connections 158 and the analog and digital and connector block interface 157 incorporating input modules. The microprocessor computer 159 preferably comprises program memory 159(A) random access memory (RAM) and read only memory (ROM), stored by a hard-drive (HD) and or erasable programmable read only memory (EPROM), software code 159(B) stored by either RAM, ROM, EPROM, or HD, and user interface 159(C) incorporating keyboard, mouse, interconnection cables and a numerical (electrical [electronic]) and graphical display (computer monitor) 159(D).

Figure 3:
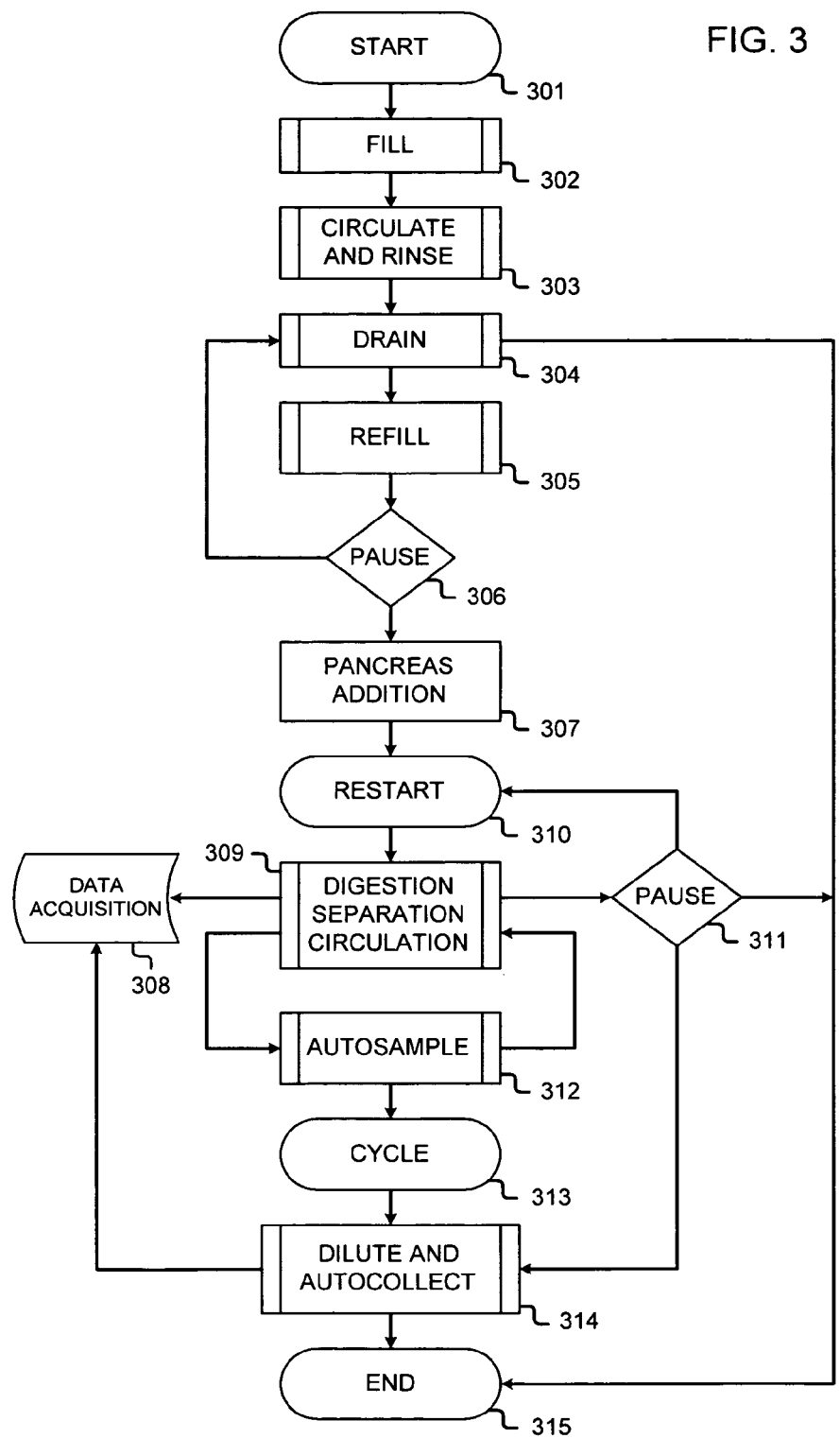
FIG. 3 is a schematic flowchart showing the sequence of operations of the automated islet separation method in the order performed by the automated islet separation apparatus according to one preferred embodiment of the invention.

FIG. 3 illustrates a schematic flowchart illustrating the automated method of islet isolation according to one preferred embodiment of the invention. Initially the automated islet isolation process is started in start step 301, the automated islet separation apparatus fills with physiologic process solution in fill step 302, the process solution is circulated and the interior of the islet separation apparatus is rinsed in circulation and rinse step 303, the process solution is drained in drain step 304, and the apparatus is refilled in refill step 305 with fresh physiologic process solution after which the automated method and automated apparatus pause in operation (flow) in first pause step 306 while pancreas addition in pancreas addition step 307 to the digestion chamber takes place. The method and apparatus are restarted in restart step 310, initiating pancreatic digestion, separation and circulation in digestion/separation/circulation step 309 of islets and processing fluid, while real-tine process data acquisition (DAQ) in data acquisition step 308 is executed. During digestion/separation/circulation step 309, autosampling step 312 is executed and the method and apparatus may be paused in second pause step 311 at any time. When sufficient numbers of islets have been liberated and separated from the pancreas into the processing solution, the method and apparatus are cycled in cycle step 313, so dilution and auto-collection step 314 is executed and when complete, islet processing ends in end step 315.

FIG. 4 illustrates the automated islet separation apparatus process control valve logic chart 401 for the automated islet separation method and automated islet separation apparatus according to one preferred embodiment of the invention. After the automated method is started in start step 301 (previously presented in FIG. 3), the islet isolation apparatus initially fills in fill step 302 with physiologic process solution while process valves 104, 116, 126, 132, 154, and 180 are open and process valves 115, 117, 125, 127, 131, 135, 137 and 153 are closed. During the circulation and rinse phase in circulation and rinse step 303 of islet processing, process valves 116, 180, 126, 132, 139, and 153 are open and process valves 104, 115, 117, 125, 127, 131, 135, 137, and 154 are closed. When the process solution is drained in drain step 304 from the apparatus process valves 104, 116, 180, 126, 132, and 137 are open and process valves 115, 117, 125, 127, 131, 135, 139, 153 and 154 are closed. The apparatus is refilled in refill step 305 with physiologic process solution with process valves 104, 116, 180, 126, 132, and 154 open and process valves 115, 117, 125, 127, 131, 135, 137 and 153 closed. Pancreas addition in pancreas addition step 307 to the dynamic flow digestion chamber 120 is accomplished while process valves 115, 125, 126, 132, 139 and 153 are open and process valves 104, 116, 117, 180, 127, 131, 135, 137, and 154 are closed. During pancreatic digestion, islet separation, and circulation in digestion/separation/circulation step 309 of the process fluid in the forward direction through the digestion chamber, process valves 116, 180, 126, 132, 139, and 153 are open and process valves 104, 115, 117, 125, 127, 131, 135, 137 and 154 are closed. Throughout pancreatic digestion, islet separation, and circulation in digestion/separation/circulation step 309 of the process fluid in the reverse direction through the digestion chamber, process valves 115, 117, 125, 180, 127, 132, 139, and 153 are open and process valves 104, 116, 126, 131, 135, 137 and 154 are closed. Auto-sampling and circulation in auto-sampling step 312 of the islet containing process fluid takes place while process valves 116, 180, 126, 132, 135, 139, and 153 are open and process valves 104, 116, 118, 126, 128, 132, 137, and 154 are closed. During dilution and auto-collection process in dilution and auto-collection step 314, valves 104, 116, 180, 126, and 131, are open and process valves 115, 117, 125, 127, 132, 135, 137, 139, 153, and 154 are closed. Dissolved oxygen is preferably displaced and removed from the process fluid by opening the helium control valve 149 and sparging the process fluid with helium from the helium tank 148. Dissolved oxygen may be added to the process solution by opening the oxygen control valve 146 and sparging the process fluid with oxygen from the oxygen tank 147.

Figure 5:
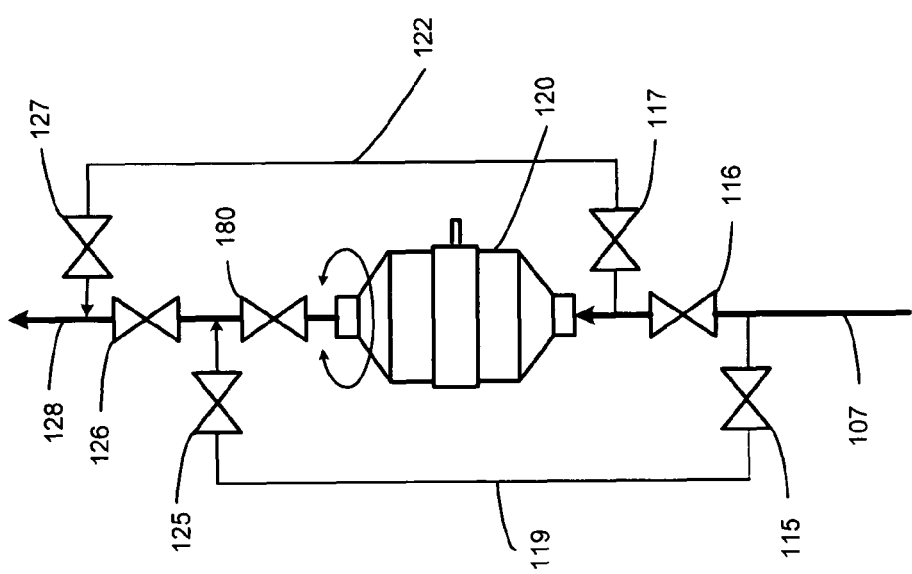
FIG. 5 is a schematic diagram of the dynamic flow digestion chamber showing the direction of forward fluid flow through the digestion chamber according to one preferred embodiment of the invention.

FIG. 5 illustrates the islet containing process solution flow in forward direction through the dynamic flow digestion chamber during pancreatic digestion, islet separation, and process solution circulation in digestion/separation/circulation step 309, (previously presented in FIG. 1, FIG. 3, and FIG. 4) according to one preferred embodiment of the invention. The process solution flows through the dynamic flow digestion chamber 120 in the forward direction while process valves 116, 180, and 126 are open and process valves 115, 117, 125, and 127 are closed.

Figure 6:
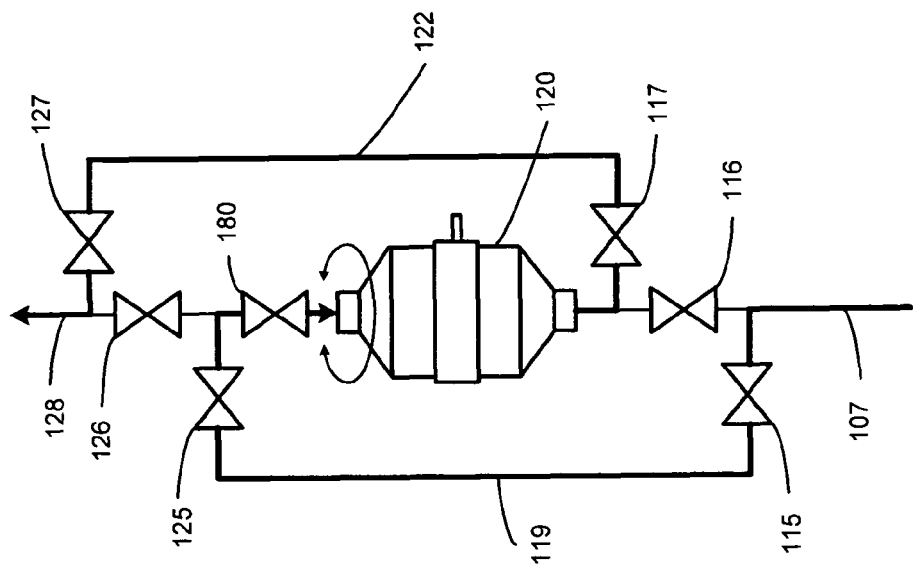
FIG. 6 is a schematic diagram of the dynamic flow digestion chamber showing the direction of reverse fluid flow through the digestion chamber according to one preferred embodiment of the invention.

FIG. 6 illustrates the islet containing process solution flow in reverse direction through the dynamic flow digestion chamber during pancreatic digestion, islet separation, and process solution circulation in digestion/separation/circulation step 309, (previously presented in FIG. 1, FIG. 3, and FIG. 4) according to one preferred embodiment of the invention. The process solution flow through the dynamic flow digestion chamber 120 in the reverse direction is achieved while process valves 115, 125, 180, 117, and 127 are open and process valves 116 and 126 are closed.

One skilled in the art would know that endotoxin concentration can be measured using the *Limulus Amebocyte* Lysate (LAL) assay and that the Pyros Kinetix instrument for performing this assay is available from Associates of CAPE COD, Inc. (WWW URL acciusa.com/lal/pyros_kinetix.html). This assay was mentioned in the Vargas et al. paper that was incorporated by reference above.

One skilled in the art would also know that endotoxin neutralizing protein (ENP) is commercially available at Associates of CAPE COD, Inc. (WWW URL acciusa.com/search.html?searchterm=pyros+kinetix, see reference 6 on this web page). ENP can also be purchased from Pharm-Canada (WWW URL pharmcanada.net/Research%20products.htm#enp).

One skilled in the art would have known that Liberase® (manufactured by Roche) is a preferred proteolytic enzyme (collagenase) for use human and porcine islet isolation. Initially, an appropriate proteolytic enzyme activity is calculated for the mass of the pancreas, so, in preferred embodiments, no more needs be added during the islet isolation process. During the dilution and collection phase of islet isolation, the proteolytic enzyme activity is preferably controlled by reducing its activity by chelating or deactivating it with an antibiotic.

Nitric oxide inhibition and scavenging improves islet survival and secretory function. In preferred embodiments, nitric oxide synthase (NOS), and subsequently nitric oxide, is inhibited by adding derivatives of L-arginine, the natural substrate of nitric oxide synthase. These include methyl-, dimethyl-, or amino-substituted guanidines. These inhibitory compounds are also chemically known as aminoguanidinie, N,N'-diaminoguanidine, methylguanidine and 1, 1-dimethylguanidine (U.S. Pat. No. 5,837,738 and U.S. Pat. No. 5,919,775, both previously incorporated herein by reference). Nitric oxide production is also preferably inhibited by adding 2,4-diamino-6-hydroxy-pyrimidine, a compound that interferes with the activity of a cofactor of inducible nitric oxide synthase. Antibiotic tetracycline addition may also be used to inhibit nitric oxide synthase, thus preventing the formation of nitric oxide, as do doxycycline, and minocycline, a semisynthetic tetracycline (U.S. Pat. No. 5,919,775, previously incorporated herein by reference). Nitric oxide may also be inhibited by adding nitric oxide scavengers such as cysteine, and other sulfated compounds such as dextran, heparin, and cystine, U.S. Pat. No. 5,834,005 (previously incorporated herein by reference). Alternatively, sparging with an inert gas such as helium may be used to effectively control and eliminate the dissolved oxygen concentration in the islet containing physiologic process solution, thereby hindering the production of nitric oxide via reduction and catalytic oxidation of L-arginine by NOS and cofactors. In combination with oxygen removal from the process solution, cysteine, dextran, heparin, and cystine may also be used to inhibit nitric oxide formation that results from relative states of islet hypoxia.

One skilled in the art would also know that sensors are commercially available that are capable of measuring dissolved oxygen, dissolved nitric oxide, and dissolved carbon dioxide. For example, a nitric oxide sensor and instrument is commercially available from World Precision Instruments, Inc. (WWW URL wpiinc.com/WPI_Web/Biosensing/Apollo.html All publications, patents, and patent documents are incorporated herein by reference, as though individually incorporated by reference. The invention has been described with reference to various specific and preferred embodiments and techniques. However, it should be understood that many variations and modifications might be made while remaining within the spirit and scope of the invention. The above descriptions of exemplary embodiments are for illustrative purposes. Because of variations that will be apparent to those skilled in the science, the present invention is not intended to be limited to the particular embodiments described above. Thus, various modifications of the above-described embodiments will be apparent to those skilled in the art or science. The present invention may also be practiced in the absence of any element not specifically disclosed. The invention may be applied to pancreatic tissue containing islets of Langerhans with insulin producing beta cells harvested from animals and mammals either transgenic or non-transgenic.

Many variations of the invention will occur to those skilled in the art. Some variations include control of a large subset of process variables. Other variations call for control of a small subset of process variables. All such variations are intended to be within the scope and spirit of the invention.

Although some embodiments are shown to include certain features, the applicants specifically contemplate that any feature disclosed herein may be used together or in combination with any other feature on any embodiment of the invention. It is also contemplated that any feature may be specifically excluded from any embodiment of the invention.

What is claimed is:

1. An apparatus for isolating islets from a pancreatic tissue, comprising:
    a heated feed tank;
    a reactor for containing a physiologic process solution having a dissolved oxygen concentration, an antibiotic concentration, a pH, a temperature, and a flowrate said reactor comprising a flow loop that connects a digestion chamber, a sparging vessel and a process pump, said flow loop being connected through a first valve to said heated feed tank, said process pump being operative to circulate said physiologic process solution through said reactor;
    a process controller;
    a sensor block that is located on said flow loop upstream from said digestion chamber, said sensor block having a plurality of sensors that send signals to said process controller, said sensor block comprising a dissolved oxygen sensor for sensing said dissolved oxygen concentration, an antibiotic sensor for sensing said antibiotic concentration, a pH sensor for sensing said pH, a temperature sensor for sensing said temperature, and a flow sensor for sensing said flowrate;
    a source of oxygen gas controlled by a oxygen gas valve for introducing a stream of oxygen gas into said sparging vessel, a source of antibiotic controlled by a pump for introducing antibiotic into the process, and a source of an inert gas controlled by an inert gas valve for introducing a stream of inert gas into said sparging vessel;
    an auto-collector that is connected to said flow loop for collecting the islets;
    an integrated flow-through sample cell for monitoring the extent of pancreatic digestion and islet separation in real-time;
    a proteolytic process controller which deactivates proteolytic enzyme activity and ends digestion by adding an effective amount of an antibiotic in response to a signal derived from said flow through sample cell; and
    wherein said process controller compares the dissolved oxygen concentration in said physiologic process solution to a dissolved oxygen setpoint and activate either said oxygen gas valve to add dissolved oxygen or said inert gas valve to remove dissolved oxygen, to compare said antibiotic concentration setpoint and activate control of antibiotic concentration, compares said pH to a pH setpoint and activate either said acid solution pump to reduce said pH or said base solution pump to increase said pH, compares said temperature to a temperature setpoint and to activate either said process cooler to decrease said temperature or said process heater to increase said temperature, and compares said flowrate to a flowrate setpoint and control said flowrate.

2. The apparatus of claim 1 wherein said plurality of solution pumps further comprise a dissolved nitric oxide control means selected from the group consisting of an antibiotic solution pump for pumping an antibiotic solution from an antibiotic solution reservoir into said flow loop, a nitric oxide scavenger solution pump for pumping a nitric oxide scavenging solution from a nitric oxide scavenger solution reservoir into said flow loop, and an amino acid solution pump for pumping an amino acid solution from an amino acid solution reservoir into said flow loop; and wherein said process controller is operative to compare said dissolved nitric oxide concentration to a dissolved nitric oxide concentration set point and activate said antibiotic solution pump, said nitric oxide scavenger solution pump or said amino acid solution pump.

3. The apparatus of claim 1 wherein moving means are provided that are operative to rotate, move linearly or move eccentrically said digestion chamber, valve means are provided that are operative to circulate the physiologic process solution through said digestion chamber in a forward direction and in a reverse direction and transducer means are provided that are operative to cause sonication of the physiologic process solution circulating through said digestion chamber.

4. The apparatus of claim 1, wherein the opening and closing of said valves is controlled by manual manipulation of said computer by a user.

5. The apparatus of claim 1, wherein said computer further comprises a graphical user interface to facilitate manual manipulation of said computer by said user.

6. The apparatus of claim 1, further comprising a flow through sample cell to monitor and control the extent of islet separation via image analysis.

7. The apparatus of claim 1 wherein said physiologic process solution further has an endotoxin concentration;
    wherein said sensor block further comprises an endotoxin sensor assembly for sensing said endotoxin concentration;
    wherein said plurality of solution pumps further comprise an endotoxin neutralizing solution pump for pumping an endotoxin neutralizing solution from an endotoxin neutralizing solution reservoir into said flow loop; and
    wherein said process controller is operative to compare said endotoxin concentration to an endotoxin concentration set point and activate said endotoxin neutralizing solution pump.

8. The apparatus of claim 2 wherein nitric acid control comprises an inert gas valve.

* * * * *